United States Patent [19]
Thayer et al.

[11] Patent Number: 6,131,209
[45] Date of Patent: Oct. 17, 2000

[54] EYEWEAR CLEANING APPARATUS

[76] Inventors: Timothy R. Thayer, 11302 Wildwood Ct., Blaine, Minn. 55449; Brett W. Frey, 10083 Kerry Ct., Hugo, Minn. 55038

[21] Appl. No.: 08/887,341

[22] Filed: Jul. 2, 1997

[51] Int. Cl.$^7$ .................................................. A61F 9/02
[52] U.S. Cl. .................................. 2/452; 2/426; 351/157
[58] Field of Search .............................. 2/452, 220, 206, 2/181, 181.6, 182.8; 351/158, 157; 206/5, 8, 278, 233, 6, 38

[56] References Cited

U.S. PATENT DOCUMENTS

| | | |
|---|---|---|
| 2,481,946 | 9/1949 | Pendleton . |
| 2,539,922 | 1/1951 | Nyberg . |
| 2,798,409 | 7/1957 | Speers . |
| 2,968,076 | 1/1961 | Chanko . |
| 3,397,026 | 8/1968 | Spina . |
| 3,502,396 | 3/1970 | Greenberg . |
| 3,647,059 | 3/1972 | Humphreys ............................. 206/278 |
| 3,827,790 | 8/1974 | Wenzel . |
| 3,874,776 | 4/1975 | Seron . |
| 3,879,804 | 4/1975 | Lawrence . |
| 4,133,604 | 1/1979 | Fuller . |
| 4,541,696 | 9/1985 | Winger . |
| 4,603,951 | 8/1986 | Beck . |
| 4,657,364 | 4/1987 | Murrell . |
| 4,696,556 | 9/1987 | Perry, III . |
| 5,014,846 | 5/1991 | Walker et al. .............................. 206/5 |
| 5,092,668 | 3/1992 | Welch . |
| 5,102,216 | 4/1992 | Mitchell ..................................... 206/5 |
| 5,151,778 | 9/1992 | Conley ....................................... 206/5 |
| 5,204,701 | 4/1993 | Chapman . |
| 5,299,682 | 4/1994 | Tartar ......................................... 206/5 |
| 5,366,072 | 11/1994 | Goldenberg . |
| 5,369,452 | 11/1994 | Williams . |
| 5,384,605 | 1/1995 | Escobosa . |
| 5,511,251 | 4/1996 | Brakas . |
| 5,593,024 | 1/1997 | Seiler ......................................... 206/5 |
| 5,687,837 | 11/1997 | Seiler ......................................... 206/5 |

*Primary Examiner*—Danny Worrell
*Attorney, Agent, or Firm*—Moore & Hansen

[57] ABSTRACT

An eyewear cleaning apparatus utilizes a flexible retaining band which has ends which engage and retain eyewear such as eyeglasses, sunglasses, goggles and the like to allow the eyewear to be carried about the neck of the user. A selectively closeable compartment is positioned on the band intermediate the ends and contains a specialized lens cleaning cloth which is moveable between an extended cleaning position confronting the lenses of the eyewear and a rolled or folded storage position within the compartment where the cloth can be effectively carried, stored and protected from contamination yet always be available for lens cleaning when needed. When in the stored position, the cloth is substantially undetectable to the casual eye, and the band retains its aesthetically attractive appearance.

16 Claims, 1 Drawing Sheet

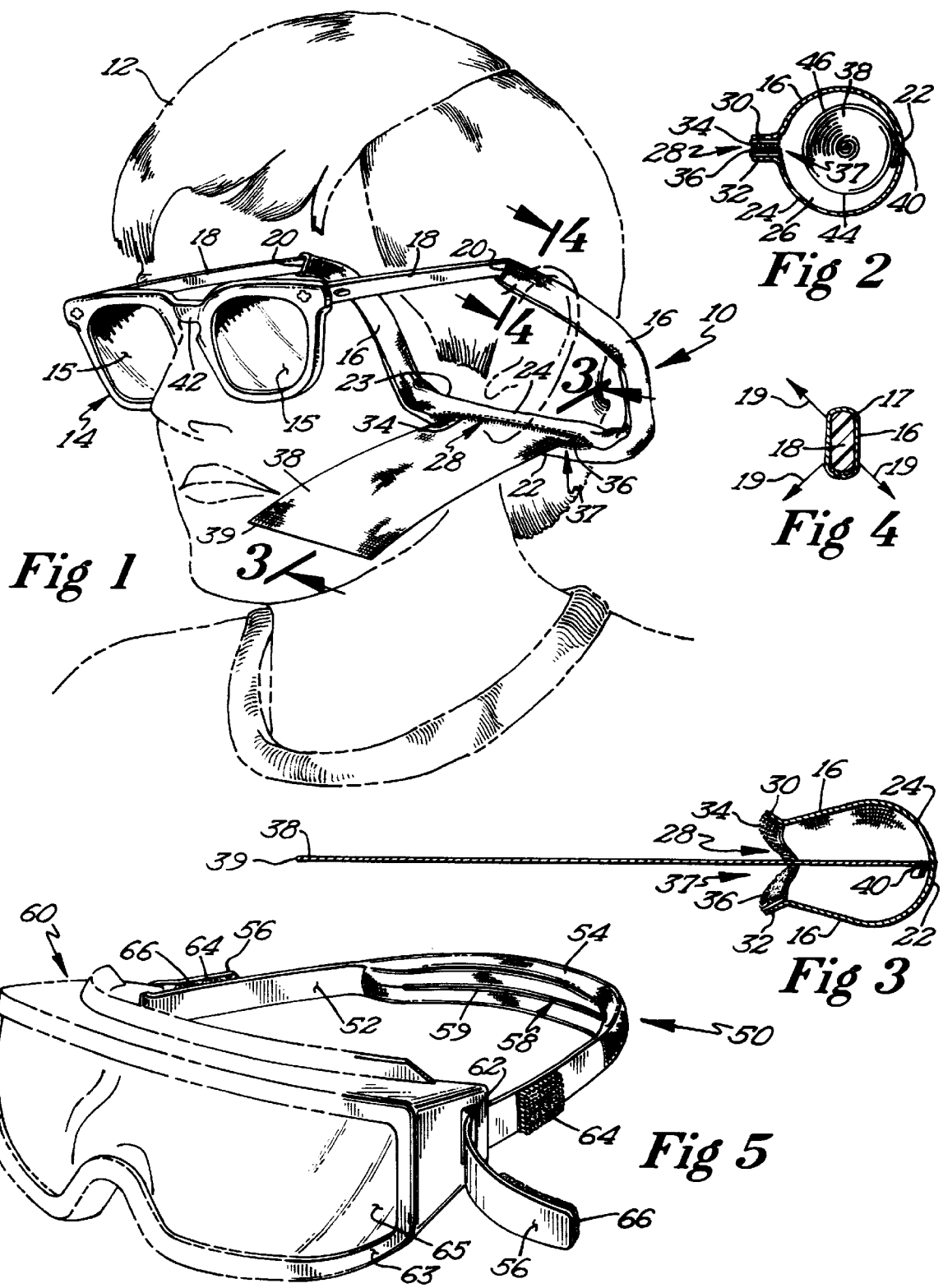

EYEWEAR CLEANING APPARATUS

BACKGROUND OF THE INVENTION

Eyewear, such as corrective eyeglasses, sunglasses, sport goggles, protective work glasses and the like, is used by virtually everyone in modern society. Beside the large numbers of people who require corrective lenses for normal vision, even those with normal vision will at times use protective glasses for hazardous work, sunglasses for eye comfort or sport glasses or goggles for skiing, shooting, cycling or other sport activity. When not being worn on the face, such eyewear is generally not convenient to carry or store. For example, unless one's clothing or handbag has sufficient pockets or space, the storing of a set of eyeglasses or goggles therein is space consuming and inconvenient. Eyewear, and particular bulky, fragile eyewear, is hard to carry or store in handbags or in the pockets of clothing, and few wish to carry the eyewear in their hands on a prolonged basis.

The foregoing problems have been partially alleviated by the use of eyewear retaining bands formed of straps or cords which pass about the neck of the user and engage the eyewear, usually attaching to the bows of the eyewear. When the user elects to remove the eyeglasses from his eyes, they can be comfortably suspended about the user's neck for reasonable times by using such retaining devices.

An accompanying annoyance associated with eyewear and which is somewhat aggravated as a result of retaining band usage is that eyewear suspended from the user's neck gathers dust, pollen, and other contaminants and requires more frequent cleaning. Because the user who carries the eyewear on a retaining band usually has few pockets or little handbag space available, such user is also unlikely to have any suitable cleaning cloth to clean the lenses of the eyewear. As a result, when the finely polished surfaces of glass or plastic eyeglasses, sunglasses or other eyewear become sufficiently dirty or contaminated that they need cleaning, often the only devices readily available for cleaning are relatively coarse handkerchiefs, paper towels, napkins or other fabrics which are so roughly textured that they may scratch or damage the lenses or lens coatings. Since many modern lenses are formed of plastic or include specialized coatings for sun control, ultraviolet filtering and the like, the surfaces of these lenses can be particularly vulnerable to damage when improper cleaning media is used.

While suitable fabrics for the cleaning of fine lenses are well known and commercially available, there is currently no convenient and unobtrusive way to carry such lens cleaning cloths so as to always have them in close proximity to the eyewear when needed and to easily keep such a lens cloth clean. If one chooses to carry such a cleaning cloth, it will usually be carried in one's pocket or purse, and the initially clean cloth quickly becomes contaminated with dirt and abrasive material or can be easily forgotten, lost or even accidentally destroyed during laundering. A device is needed to keep such a lens cleaning cloth available with one's eyewear, to assure that the cloth is protected from dirt and contamination until needed, and to store the cloth conveniently and preferably unobtrusively.

Many eyewear retaining devices are known, but perform only a retaining function by holding the eyewear on the user's head or about his neck. U.S. Pat. No. 5,384,605 discloses the use of an eyeglass retaining band to also carry a sweat band. U.S. Pat. No. 5,092,216 to Troy E. Mitchell teaches the inclusion of a stretchable eyeglass case in the center region of a retaining strap. U.S. Pat. No. 5,366,072 to Goldenberg discloses the use of a retaining strap which includes a pouch positioned intermediate the ends of the strap and into which the eyeglasses can be stored or other small items such as keys or money may be inserted. None of the prior patents suggest or disclose any cleaning apparatus which may be conveniently, protectively and unobtrusively stored in association with an eyewear retaining band so as to be readily available for use with one's eyewear.

SUMMARY OF THE INVENTION

The invention relates to eyewear retaining bands used for the carrying of eyeglasses about the head or neck of a user and provides a compartment positioned intermediate between the ends of the retaining band and in which a lens cleaning cloth may be carried.

The compartment has an access aperture confronting the eyewear and equipped with a closure device such as a hook and pile closure. The closure device effectively seals the compartment against the intrusion of dust, pollen and other contaminants, keeping the compartment and the stored eyewear cleaning cloth clean and protected.

The cleaning cloth may be moved from a stored position, wherein the cloth is rolled or folded within the compartment, to a fully extended position, wherein the cloth is extended toward the eyewear and available for cleaning of the eyewear lenses. The selectively closeable compartment permits the cleaning cloth to be stored immediately adjacent the eyewear for convenient use when needed yet wholly protected within the compartment from unwanted contamination. In addition, the cleaning cloth, when rolled or folded to a stored position is literally enveloped by the retaining band, and is thus so effectively hidden from external view that an observer would detect no tell-tale bulges or irregularities which would suggest that the band was storing an object therein.

Accordingly, the invention provides a mechanism by which a cleaning cloth may be always kept available in close proximity to one's eyewear, while maintaining it in a safe, clean and unobtrusive location which has no adverse impact on the sleek line or otherwise attractive contour of an eyewear retaining band.

These and other objects and advantages of the invention will be readily understood by reading the following description in conjunction with the accompanying figures of the drawings wherein like reference numerals have been applied to designate like elements throughout the several views.

BRIEF DESCRIPTION OF THE DRAWINGS

FIG. 1 is a front perspective view of a first embodiment of an eyewear cleaning apparatus attached to a pair of eyeglasses and in which the lens cleaning cloth is shown in extended position and a user of the device is shown in phantom.

FIG. 2 is a cross sectional side view taken through the intermediate region of the retaining band of FIG. 1 and showing a cleaning cloth in a rolled, stored position within the band.

FIG. 3 is a cross sectional side view of the cleaning apparatus of FIG. 1 taken along cutting plane 3—3 and showing the cleaning cloth in an extended position.

FIG. 4 is a cross sectional side view of the cleaning apparatus of FIG. 1 taken along cutting plane 4—4 and illustrating the manner in which the apparatus may be attached to a bow of a pair of eyeglasses.

FIG. 5 is a perspective view of a second embodiment of an eyewear cleaning apparatus shown in use with a set of goggles.

DESCRIPTION OF THE PREFERRED EMBODIMENTS

Referring now to FIG. 1, a first embodiment 10 of an eyewear cleaning apparatus in accord with the invention is shown in wearing position on the head of a user 12 and attached to eyewear 14, here shown as a pair of conventional eyeglasses having lenses 15, which may be made of glass or a plastic lens material.

The eyewear cleaning apparatus 10 includes a flexible eyewear retaining band 16 which is used to retain the eyewear about the head or neck of the user. In the embodiment 10, the band 16 is formed of a natural or synthetic fabric formed to have an elongated tubular cross section 17 best seen in FIG. 4. The band is preferably formed of a material which has an elastic characteristic such that the tubular band can be radially, elastically expanded in directions 19 (FIG. 4) from the center of its tubular cross section so as to permit temporary enlargement of the cross section sufficiently to allow the end of each bow 18 of the eyewear to be inserted within the open and radially stretched tubular end 20 of the band. After insertion of each bow within an end 20, the elastic characteristic of the band tends to effectively cause the band to radially contact, engage and frictionally retain the bow 18 within the band so as to releaseably clamp the band onto the bow. The use of a flexible and elastic tubular material for retaining the bows of eyeglasses within a retaining band is known to the art as a means to suspend eyeglasses from the neck of a user.

Referring now to FIGS. 1–3 of the drawing, the retaining band 16 carries a storage compartment 24 positioned between the ends 20 of the band in intermediate region 22. The compartment may be formed in any known way and has an interior 26. One preferred way in which the compartment 24 may be constructed is by stitching or forming the band 16 into a tubular body beginning at each end 20 of the band with such stitching extending toward the intermediate region 22, but allowing the intermediate region of the tubular band to be unstitched to allow the unstitched portion to define an entry aperture 28 for the compartment 24. As best shown in FIGS. 2 and 3, the aperture 28 has upper and lower lips 30 and 32, respectively. Stitched to the upper and lower lips 30 and 32, respectively, are hook portion 34 and pile portion 36, respectively, of a closure device 37 of the type commonly sold under the Velcro trademark. The closure device 37 allows the compartment to be securely closed to substantially prevent contaminants such as dust, pollen, sweat and the like from accumulating within the compartment 24 or contaminating the cleaning cloth 38, described hereafter.

Referring now to FIGS. 1 and 3 a lens cleaning cloth 38 is fixed to the interior 26 of the compartment 24 and is shown in an extended position 39 wherein the cloth may be used to clean the front and rear surfaces of the lenses 15 of the eyewear 14.

While the cleaning cloth 38 may be carried by the band 16 by loosely storing the cloth within the compartment 24 without it being attached to band or compartment, it is preferred to attach the cloth to the band generally or to attach the cloth within the compartment, preferably by stitching 40 so as to prevent accidental loss of the cleaning cloth 38 and to assure that it is always available with the band. Both loose, unattached carrying of the cloth 38 within compartment 24 or alternatively its being attached to the band or compartment are within the purview of the invention.

It is desired to position the compartment 24 and cloth 38 approximately intermediate between the ends 20 of the band so as to cause the cleaning cloth to directly confront the central bridge 42 and lenses 15 of the eyewear and to have the cleaning cloth in the most advantageous location for convenient cleaning of both lenses 15.

While a variety of fabrics may be used for the cleaning cloth 38, it is preferred that the cloth be a soft fabric which is designed for non-injurious cleaning of the surface of glass or plastic lenses and for cleaning of the specialized lens coatings sometimes applied to lenses. Various high density fine weave blends of polyester and nylon material are commercially available for the cleaning of lenses and are useable with the invention.

One type of cleaning cloth useable with the invention is a fabric formed of 75% polyester and 25% nylon sold by Karlen Manufacturing, Inc. under the trademark Ultra Clear. Other effective cleaning cloths have been formed of fine soft weaves of cotton, polyester, nylon or silk materials or combinations thereof. Any known lens cleaning cloth may be used with the invention.

When the cleaning cloth 38 is not being used for cleaning of eyewear, it is desirable to keep it stored in a location secure from contaminants. The invention stores the cloth 38 in compartment 24 where it is always available for use but safe from contaminants. The cloth may be either simply folded or alternatively, rolled into a tight spiral 44 as shown in FIG. 2 and then placed in the stored position 46 within interior 26 of the compartment 24. The upper and lower lips 30 and 32 may then be brought together with the hook and pile closure 37 providing a reliable closure device to prevent the unwanted entry of contaminants such as dirt, dust, pollen and perspiration from the user. By providing a tightly sealed compartment 24, the cloth 38 is effectively isolated from contaminants. By rolling the cloth in a tight spiral 44, the cloth is further protected against contamination, and storage space is optimally conserved. If at times the user does not wind the spiral tightly, the elastic nature of the cross section of the band 16 tends to compress the spiral 44 and to thereby keep the cross sectional size of the band generally uniform and regular. FIG. 2 shows the cleaning cloth in a stored position 46. If it is desired to utilize a larger size cleaning cloth, the band 16 may be formed with its intermediate region 22 having a slightly larger cross section to produce a larger compartment for accommodating the larger cloth.

While a specific form of a compartment 24 has been shown in which the compartment is an integral part of the band 16, it should be understood that an enclosure separate from the band could define the compartment and be carried on or attached to the retaining band in any known way. Such an alternative is within the purview of the invention.

Referring now to FIG. 4, it will be seen that the elasticized cross section of the band 16 tends to tightly engage each bow 18 of the eyewear to thereby attach the apparatus 10 to the eyewear to prevent inadvertent separation of eyewear and band. While the cleaning apparatus 10 has been shown with a band which engages the eyeglasses by an elastic frictional action, it should be understood that the invention is not limited to use with an elasticized band. The band may engage and retain the eyewear in any known way which allows the band to be attached to the eyewear and suspended about the head or neck of the user, and all such alternatives are within the purview of the invention. Such eyewear may include conventional eyeglasses, sunglasses, protective working or sport glasses, goggles or other specialty eyewear.

Referring now to FIG. 5, a second embodiment 50 of the invention shows the invention in use with a set of protective goggles 60 of the type used for skiing and other activities. The embodiment 50 utilizes a flexible eyewear retaining band 52 which may be formed of any suitable material and which includes a compartment 54 positioned in the intermediate region between the ends 56 of the band and having an access aperture 58 to the interior of the compartment 54. The access aperture 58 is provided with a closure device 59 such as a hook and pile closure to allow the aperture to be selectively opened or closed. Any suitable closure device may be used and is within the purview of the invention.

In embodiment 50, the ends 56 of the band engage the eyewear, here shown as goggles 60 by passing through an upright slot 62 in the goggles' frame 63 and then being secured to the band by a hook and pile closure device utilizing hook portion 64 and pile portion 66. While a hook and pile closure is shown, it should be understood that any other means of attachment to the goggles may be substituted and is within the scope of the invention.

Positioned within compartment 54 is an extendable lens cleaning cloth 38 like that described earlier in association with embodiment 10 and which preferably has one end of the cloth fixed to the interior of the compartment 54. The cleaning cloth 38 of embodiment 60 may be extended outward from the compartment 54 toward frame 63 to allow the cloth to be used to clean front and rear surfaces of the lens 65. The entry aperture 58 will be opened during such extending and is closed when the cleaning cloth is stored in the compartment 54. Thus the cloth 38 can be kept in a clean, uncontaminated storage position 46 where it is unobtrusive and out of the way yet immediately available when needed.

In operation, when the user wishes to use the cleaning apparatus 10, the user first attaches the ends 20 of the flexible retaining band 16 to the bows 18 of the eyewear. With embodiment 10 shown in FIG. 1 such attachment would be accomplished by slipping the ends of each bow 18 into the tubular openings at the ends 20 of the band and allowing the flexible elasticized band contract and to tightly engage and frictionally retain each bow. Embodiment 50 is attached by passing each end 56 of the band 52 through slots 62 of the goggles frame 63 and then closing the hook and pile closure 64,66 on the band.

When it is desired to clean the lenses of the eyewear, the user pulls the hook and pile portions of access aperture 28 or 58 apart to open the entry aperture of compartment 24 or 54, respectively. The user will then pull the cleaning cloth 38 from its stored position 46 to its extended position 39 wherein the cloth extends toward and confronts the lenses of the eyewear. The user may then rub the lens with the cleaning cloth 38 to clean and polish the lens surfaces without damage to any lens. When the cleaning process has been completed, the user rolls the cleaning cloth into a spiral 44 or folds it to a stored position 46 and places it back within the interior of the compartment 24 or 54. The user then closes the entry aperture of the compartment by pushing the hook portion and pile portion of the closure tightly together. With the compartment closed as shown in FIG. 2 and FIG. 5, contaminants are excluded from the compartment, and the lens cleaning cloth 38 is kept clean and protected for future uses. The stitching of the cloth 38 to the interior of the compartment assures that the cloth is not easily separated from the compartment or lost, thus making the cloth continually available for cleaning. By storing the cloth with the band, the cloth need not be carried in a handbag or pocket by the user and subjected to the risk of loss or contamination by other items contained within the handbag or pocket. The invention allows the cleaning cloth to be stored inconspicuously in a portion of the band which would otherwise be wasted space and does not compromise the appearance of the band.

It is anticipated that various changes, variations and modifications may be made in the construction, arrangement, operation and method of construction of the invention disclosed herein without departing from the spirit and scope of the invention as defined in the following claims.

What is claimed is:

1. An eyewear cleaning apparatus useable with eyewear having at least one lens, such cleaning apparatus being wearable about the head or neck of a user so as to be available to remove contaminants from the eyewear, comprising:
   a flexible eyewear retaining band having first and second ends, said ends being attachable to the eyewear so as to retain the eyewear on the user when said band is placed about the head or neck of the user, thereby preventing loss of the eyewear; and
   a lens cleaning cloth carried by said retaining band, said cleaning cloth including a cleaning surface constructed to clean the lens of the eyewear without destructive scratching and abrasion of the lens.

2. The eyewear cleaning apparatus of claim 1 wherein said retaining band includes a protective compartment for storing of said lens cleaning cloth, said compartment being resistant to the entry of contaminants to provide substantially clean storage of said lens cleaning cloth in said compartment.

3. The eyewear cleaning apparatus of claim 2 wherein said compartment has an access aperture and said aperture is selectively closeable to substantially prevent entry of the contaminants.

4. The eyewear cleaning apparatus of claim 2 wherein said compartment includes an access aperture and a closure device adjacent said aperture to substantially close said compartment against entry of contaminants.

5. The eyewear cleaning apparatus of claim 2 wherein said compartment is selectively closeable, and when closed, is elongated, tubular, and substantially coincident with said retaining band to store said cleaning cloth within said tubular compartment.

6. The eyewear cleaning apparatus of claim 5 wherein said cleaning cloth is attached to said retaining band to prevent accidental separation and loss of said cloth from said band.

7. The eyewear cleaning apparatus of claim 6 wherein said cleaning cloth is attached to said compartment.

8. The eyewear cleaning apparatus of claim 7 wherein said compartment has an interior and said cleaning cloth is attached to said interior of said compartment.

9. The eyewear cleaning apparatus of claim 6 wherein said cloth is sewn to said band.

10. The eyewear cleaning apparatus of claim 6 wherein said cleaning cloth is fixed to said retaining band substantially intermediate said first and second ends of said band so as to place said cleaning cloth in proximity to the lens of the eyewear when said band is attached to said eyewear.

11. The eyewear cleaning apparatus of claim 1 wherein said cleaning cloth is fixed to said retaining band substantially intermediate said first and second ends of said band so as to place the cleaning cloth in proximity to the lens of the eyewear when said band is attached to said eyewear.

12. The eyewear cleaning apparatus of claim 2 wherein said compartment has an interior, and said lens cleaning cloth is attached to said interior.

13. The eyewear cleaning apparatus of claim 12 wherein said cloth is sewn to said compartment.

14. The eyewear cleaning apparatus of claim 1 and further including a compartment on said band, and wherein said cleaning cloth is attached to said compartment and moveable between a first position, wherein said cloth is extended outward from said compartment, and a second position, wherein said cloth is substantially within said compartment.

15. The eyewear cleaning apparatus of claim 1 wherein said band includes a compartment therealong for storing said cloth, and said band is elasticized to allow said ends of said band to encircle and grip the eyewear and to allow said compartment to compress said cleaning cloth when stored within said compartment.

16. An eyewear cleaning apparatus useable with eyewear having at least one lens, such cleaning apparatus being wearable by a user so as to be available to remove contaminants from the eyewear, comprising:

a flexible eyewear retaining band having first and second ends, said ends being attachable to the eyewear so as to retain the eyewear on the user when said band is placed about the user; and a lens cleaning cloth carried by said retaining band, said cleaning cloth including a cleaning surface constructed and arranged to clean the lens of the eyewear.

* * * * *